US00PP36508P2

(12) United States Plant Patent
van Dijk

(10) Patent No.: US PP36,508 P2
(45) Date of Patent: Feb. 25, 2025

(54) ***ANTHURIUM* PLANT NAMED 'AN2729837'**

(50) Latin Name: *Anthurium andreanum*
Varietal Denomination: AN2729837

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/817,112

(22) Filed: Aug. 27, 2024

(51) Int. Cl.
*A01H 6/00* (2018.01)
*A01H 5/02* (2018.01)

(52) U.S. Cl.
USPC ..... Plt./369

(58) Field of Classification Search
USPC ..... Plt./369
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Anthurium* plant named 'AN2729837', characterized by its upright to outwardly arching and uniform plant habit; freely clumping growth habit; bushy and dense plants; narrowly cordate dark green-colored leaves; freely flowering habit; inflorescences that are positioned within to slightly above the foliar plane on strong and mostly upright scapes; broadly cordate glossy bright red-colored spathes and yellow-colored spadices; and durable spathes that impart good inflorescence longevity.

2 Drawing Sheets

Figure 1:
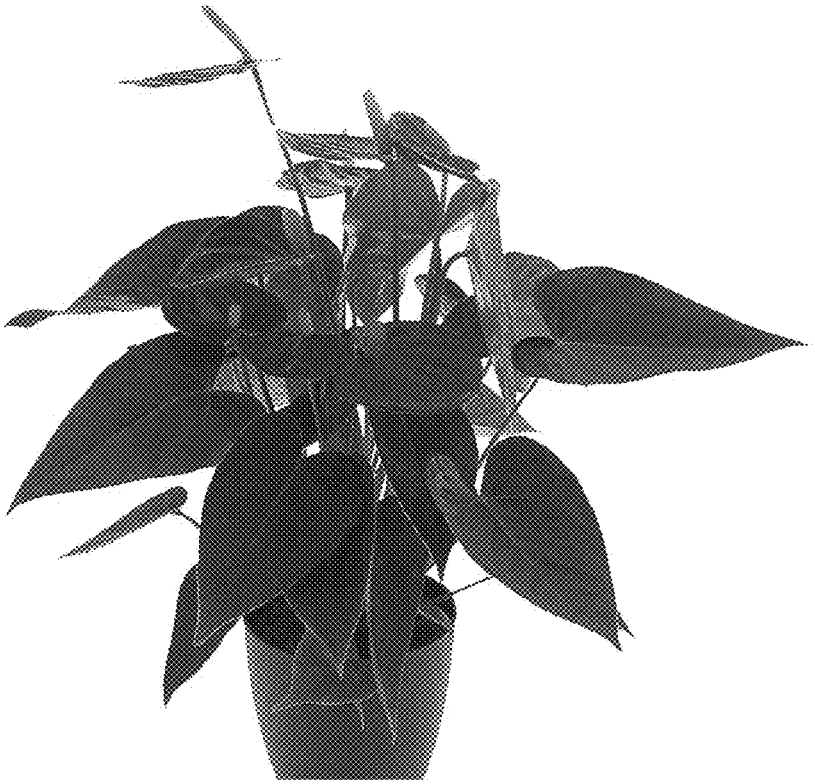

Botanical designation: *Anthurium andreanum.*
Cultivar denomination: 'AN2729837'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B.V. of Bleiswijk, The Netherlands on Nov. 22, 2023, application number 2023/2442. Foreign priority is not claimed to this application.

BACKGROUND OF THE INVENTION

The present invention relates to a new and distinct cultivar of *Anthurium* plant, botanically known as *Anthurium andreanum* and hereinafter referred to by the name 'AN2729837'.

The new *Anthurium* plant is a product of a controlled breeding program conducted by the Inventor in Bleiswijk, The Netherlands. The objective of the breeding program is to create new medium-sized and freely-clumping *Anthurium* plants with attractive and durable glossy red-colored spathes.

The new *Anthurium* plant originated from a cross-pollination made by the Inventor in July 2015 in Bleiswijk, The Netherlands of *Anthurium andreanum* 'Anthfuwio', disclosed in U.S. Plant Pat. No. 31,059, as the female, or seed, parent with a proprietary selection of *Anthurium andreanum* identified as code number 12-028233-0004, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in May 2017.

Asexual reproduction of the new *Anthurium* plant by in vitro meristem propagation in a controlled environment in Bleiswijk, The Netherlands since May 2017 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2729837'. These characteristics in combination distinguish 'AN2729837' as a new and distinct *Anthurium* plant:

1. Upright to outwardly arching and uniform plant habit.
2. Freely clumping growth habit; bushy and dense plants.
3. Narrowly cordate dark green-colored leaves.
4. Freely flowering habit.
5. Inflorescences that are positioned within to slightly above the foliar plane on strong and mostly upright scapes.
6. Broadly cordate glossy bright red-colored spathes and yellow-colored spadices.
7. Durable spathes that impart good inflorescence longevity.

Plants of the new *Anthurium* differ primarily from plants of the female parent, 'Anthfuwio', in the following characteristics:

1. Spathes of plants of the new *Anthurium* are bright red in color whereas spathes of plants of 'Anthfuwio' are orange in color.

2. Apices of spathes of plants of the new *Anthurium* are broadly and abruptly acute with a mucronate apex whereas apices of spathes of plants of 'Anthfuwio' are rounded with an acuminate apex.

Plants of the new *Anthurium* differ primarily from plants of the male parent selection in the following characteristics:

1. Plants of the new *Anthurium* are smaller than plants of the male parent selection.
2. Leaves of plants of the new *Anthurium* are shorter than leaves of plants of the male parent selection.
3. Spadices of plants of the new *Anthurium* are shorter than spadices of plants of the male parent selection.

Plants of the new *Anthurium* can also be compared to plants of *Anthurium andreanum* 'Anthgowl', disclosed in U.S. Plant Pat. No. 32,791. In side-by-side comparisons, plants of the new *Anthurium* differ primarily from plants of 'Anthgowl' in the following characteristics:

1. Plants of the new *Anthurium* are more freely clumping than plants of 'Anthgowl'.
2. Apices of spathes of plants of the new *Anthurium* are broadly and abruptly acute with a mucronate apex whereas apices of spathes of plants of 'Anthgowl' are obtuse with a broad acuminate apex.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2729837' grown in a container.

Figure 2:
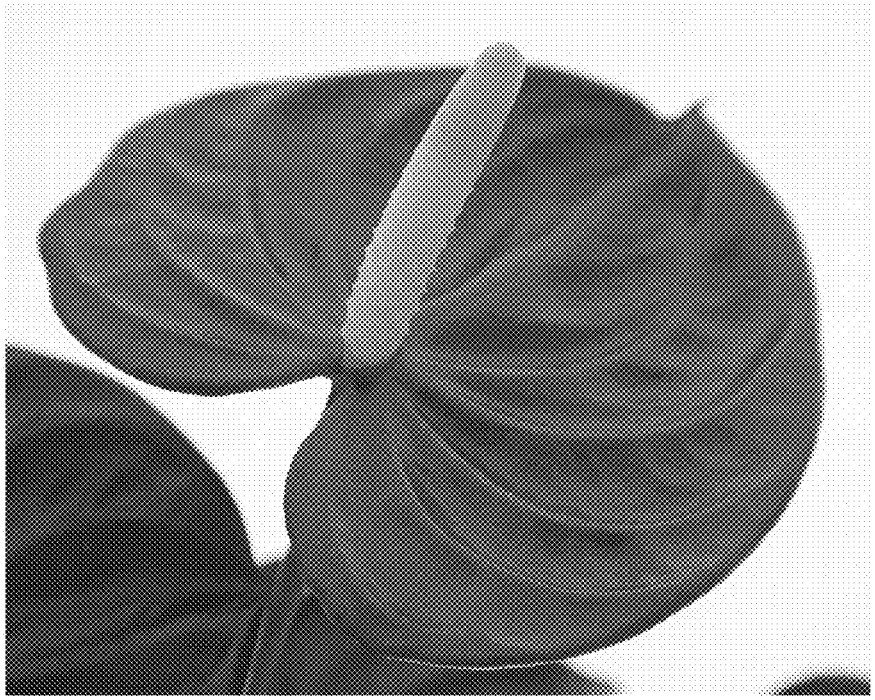

The photograph on the second sheet (FIG. 2) is a close-up view of a typical inflorescence of 'AN2729837'.

DETAILED BOTANICAL DESCRIPTION

The aforementioned photographs and following observations and measurements describe plants grown in 9-cm containers during the summer in a glass-covered greenhouse in Bleiswijk, The Netherlands. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were nine months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2729837'.

Parentage:

*Female, or seed, parent.*—*Anthurium andreanum* 'Anthfuwio', disclosed in U.S. Plant Pat. No. 31,059.

*Male, or pollen, parent.*—Proprietary selection of *Anthurium andreanum* identified as code number 12-028233-0004, not patented.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically creamy white slightly tinged with pink in color, actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading and uniform plant habit; overall shape, broadly obovate to oblong.

*Growth habit.*—Freely clumping habit with about six clumps developing per plant imparting a bushy and dense appearance; moderately vigorous growth habit and slow growth rate.

*Plant height, from soil level to top of leaf plane.*—About 22 cm.

*Plant height, from soil level to top of inflorescences.*—About 26.6 cm.

*Plant diameter or spread.*—About 29.8 cm.

Leaf description:

*Arrangement.*—Alternate; simple; about three leaves per clump.

*Length.*—About 12.7 cm.

*Width.*—About 7.6 cm.

*Shape.*—Narrowly cordate.

*Apex.*—Apiculate with a short mucronate tip.

*Base.*—Cordate; basal lobes free.

*Margin.*—Entire; not undulate to slightly and coarsely undulate.

*Texture and luster, upper and lower surfaces.*—Smooth, glabrous; moderately coriaceous; glossy.

*Venation pattern.*—Pinnate.

*Color.*—Developing leaves, upper surface: Close to 146A. Developing leaves, lower surface: Close to 146B. Fully expanded leaves, upper surface: Close to 147A; narrow marginal edges, close to a blend of 145A and 146D; venation, close to 144A. Fully expanded leaves, lower surface: Close to a blend of 146A and 146B; narrow marginal edges, close to 145A; venation, close to N144C.

*Petioles.*—Length: About 11.6 cm. Diameter: Distally, about 3 mm; proximally, about 4 mm. Strength: Strong. Texture and luster, upper and lower surfaces: Smooth, glabrous; slightly glossy. Color, upper surface: Close to 144A. Color, lower surface: Close to 144B; towards the base, tinged with close to 63B. Geniculum length: About 1.6 cm. Geniculum diameter: About 3 mm by 3 mm. Geniculum texture, upper and lower surfaces: Smooth, glabrous. Geniculum color, upper surface: Close to 144A; occasionally tinged with close to 176B. Geniculum color, lower surface: Close to 144C; towards the base, occasionally tinged with close to 173B; towards the leaf blade, occasionally tinged with close to 151A. Wing length: About 1.2 cm. Wing diameter: About 3.5 mm. Wing color: Close to 63B; distally, close to 144B.

Inflorescence description:

*Inflorescence arrangement and flowering habit.*—Spathes with spadices held within and slightly above the foliar plane on strong and erect scapes; flowering structures arise from leaf axils; freely and continuous flowering year-round in controlled temperature greenhouses in The Netherlands; typically about eleven developing and developed inflorescences per plant at one time; inflorescence development commences about 2.5 to 3.5 months after planting.

*Inflorescence longevity.*—Depending on temperature, spathes maintain good substance for about two months on the plant; inflorescences persistent.

*Fragrance.*—None detected.

*Spathes.*—Length: About 7.4 cm. Width: About 7.5 cm. Shape: Broadly cordate; flat to slightly concave. Apex: Broadly and abruptly acute with a mucronate apex. Base: Cordate. Margin: Entire; not undulate. Aspect: About 85° from the scape axis. Texture and luster, upper and lower surfaces: Smooth, glabrous; moderately coriaceous; rugose; glossy. Color: When developing, front surface: Close to 45B; at the apex, close to 46A. When developing, rear surface: Close to 48A; towards the margins, close to 46B; at the apex, close to 153C. Fully developed, front surface: Close to 46B; towards the margins, close to 46A; at the apex, close to 151B; with subsequent development, colors becoming closer to 46A, towards the base, close to a blend of 46A and 46B and at the apex, close to 18A; venation, similar to lamina colors. Fully developed, rear surface: Close to 47C; towards the base, close to 152B; at the apex, close to 151B; with subsequent development, colors becoming closer to 51C, towards the base, close to a blend of 162D and N170D and at the apex, close to 26B; venation, similar to lamina colors.

*Spadices.*—Length: About 2.8 cm. Diameter: About 8 mm. Shape: Columnar, slightly tapering towards the apex; apex, obtuse; base, obtuse; in cross-section, rounded. Aspect: About 65° from the spathe axis and about 20° from the scape axis. Color: Immature: Close to 21B; towards the apex, close to 12A. Mature: Close to 13B. Flowers: Type: Hermaphroditic. Quantity per spadix: Numerous, about 135. Height: Less than 0.5 mm. Diameter: About 2.75 mm. Shape: Roughly square. Anther color: Close to 13B. Pollen amount: Scarce. Pollen color: Close to 155D. Stigma color: Close to 13B.

*Scapes.*—Length: About 21.1 cm. Diameter: About 3 mm. Strength: Strong. Aspect: About 13° from vertical. Color: Close to a blend of N144C and N144D; distally, occasionally tinged with close to 174A.

*Seed and fruit.*—To date, seed and fruit development has not been observed on plants of the new *Anthurium.*

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2729837' as herein illustrated and described.

* * * * *